(12) United States Patent
Ito (10) Patent No.: US 10,039,511 B2
(45) Date of Patent: Aug. 7, 2018

(54) BREAST TOMOGRAPHY SYSTEM

(71) Applicant: CANON KABUSHIKI KAISHA, Tokyo (JP)

(72) Inventor: Nobuhiro Ito, Yamato (JP)

(73) Assignee: Canon Kabushiki Kaisha, Tokyo (JP)

( * ) Notice: Subject to any disclaimer, the term of this patent is extended or adjusted under 35 U.S.C. 154(b) by 59 days.

(21) Appl. No.: 14/961,463

(22) Filed: Dec. 7, 2015

(65) Prior Publication Data

US 2016/0157801 A1 Jun. 9, 2016

(30) Foreign Application Priority Data

Dec. 9, 2014 (JP) ................................. 2014-249441
Oct. 30, 2015 (JP) ................................. 2015-215255

(51) Int. Cl.
*A61B 6/00* (2006.01)
*A61B 6/03* (2006.01)
*A61B 6/04* (2006.01)

(52) U.S. Cl.
CPC .............. *A61B 6/502* (2013.01); *A61B 6/032* (2013.01); *A61B 6/0435* (2013.01)

(58) Field of Classification Search
CPC ....... A61B 6/502; A61B 6/037; A61B 6/4021; A61B 6/0457; A61B 6/587; A61B 6/4476; A61B 6/035
USPC .......... 78/21, 23, 24, 25, 26, 27, 37, 39, 119
See application file for complete search history.

(56) References Cited

U.S. PATENT DOCUMENTS

| 2004/0081273 | A1 | 4/2004 | Ning | |
| 2012/0051502 | A1* | 3/2012 | Ohta | A61B 6/00 378/37 |
| 2012/0219109 | A1* | 8/2012 | Albanese | A61B 6/02 378/37 |
| 2016/0228076 | A1* | 8/2016 | Utsumi | A61B 6/02 |
| 2016/0228083 | A1* | 8/2016 | Tamura | A61B 6/032 |

* cited by examiner

*Primary Examiner* — Don Wong
(74) *Attorney, Agent, or Firm* — Canon U.S.A., Inc. IP Division (57) ABSTRACT

A breast tomography system includes an X-ray generation tube including a reflection type target, an X-ray detector facing the X-ray generation tube with an imaginary rotation axis placed therebetween, and a gantry that stores the X-ray generation tube and the X-ray detector and that includes a front panel on the subjectee side. A tube axis of the X-ray generation tube is disposed to extend along the front panel.

25 Claims, 9 Drawing Sheets

FIG. 9 ately, a tomography sys-

BREAST TOMOGRAPHY SYSTEM

BACKGROUND

Field

Aspects of the present invention generally relates to a tomography system in which computed tomography (CT) is performed, particularly relates to a breast tomography system used to photograph a breast.

Description of the Related Art

In recent years, mammography apparatuses that take X-ray transmission images of breasts have been used for breast cancer tests. However, since images obtained by using the mammography apparatus are plan-view images, a tumor or a calcareous portion overlapping with tissue such as a mammary gland makes it difficult to detect an abnormal portion in some cases. There is known a breast tomography system that obtains a tomographic image of a breast by using the computed tomography to solve such a problem with a plan-view image.

The Specification of U.S. Patent Application Publication No. 2004/0081273 discloses a breast tomography system including an X-ray generation tube, an X-ray detector, and a gantry. The X-ray generation tube and the X-ray detector face each other and rotate around the imaginary rotation axis. The gantry stores the X-ray generation tube and the X-ray detector. The Specification of U.S. Patent Application Publication No. 2004/0081273 discloses that the X-ray generation tube is operated in such a manner that a breast is exposed to a cone beam at predetermined rotation angles to be irradiated with the cone beam. A plurality of X-ray transmission images are subsequently obtained by using the X-ray detector facing the X-ray generation tube and are subjected to reconfiguration, and a tomographic image of the breast is thereby obtained.

Note that the Specification of U.S. Patent Application Publication No. 2004/0081273 describes the X-ray generation tube including a rotary anode target and a circular pipe housing accommodating the X-ray generation tube and discloses that the tube axis of the X-ray generation tube and the longitudinal side of the housing are disposed to be perpendicular to a test bed.

However, the breast tomography system described in the Specification of U.S. Patent Application Publication No. 2004/0081273 discloses that a dead space of several tens of millimeters is produced between an emission window of the X-ray generation tube and a front panel of the gantry. The problem of the dead space is to be solved because the dead space causes a blind length, within which an X-ray transmission image is not obtained, on the chest side of the breast or causes unnecessary exposure of the chest to the X-ray through openings communicating with breast insertion portions.

The breast tomography system described in the Specification of U.S. Patent Application Publication No. 2004/0081273 provides a way of reducing the blind length in such a manner that recesses are disposed around the openings of the test bed. However, since an unnatural photographing posture of the subjectee is required to meet the recess shape of the front panel, further improvement in usability and further reduction in the blind length have been desired.

SUMMARY

An aspect of the present invention provides a breast tomography system that achieves both the usability for the subjectee and securing the photographing field on the chest side of a breast.

Another aspect of the present invention provides a breast tomography system including an X-ray generation tube including a reflection type target and an electron emission source, the reflection type target being irradiated with an electron and generating an X-ray, the electron emission source irradiating the reflection type target with an electron beam, an X-ray detector that detects the X-ray emitted from the reflection type target and transmitted through a breast, a gantry having a storing space in which the X-ray generation tube and the X-ray detector are stored and a front panel between the storing space and a subjectee, a rotation drive unit that rotates the X-ray generation tube around an imaginary rotation axis, and a breast insertion portion configured to be communicated through an opening provided in the front panel, wherein the X-ray generation tube is secured to the rotation drive unit to allow a tube axis of the X-ray generation tube to extend along the front panel.

Further features of the present disclosure will become apparent from the following description of exemplary embodiments with reference to the attached drawings.

DESCRIPTION OF THE EMBODIMENTS

Hereinafter, exemplary embodiments will be described by using the drawings. However, the present invention is not limited to the embodiments. Note that well-known or publicly-known technology is appropriately applied to components that are not particularly illustrated or not described in the Specification for the present application.

First Embodiment

First, a first embodiment of the present invention will be described by using FIGS. 1A, 1B, 1C, and 1D.

Figure 1A:
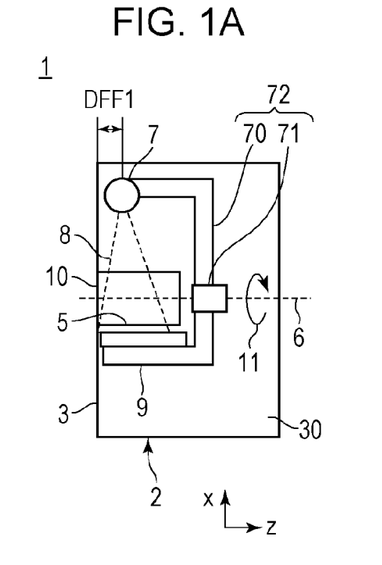
FIGS. 1A, 1B, and 1C are views illustrating a breast tomography system according to a first embodiment viewed from three angles, respectively.
Figure 1B:
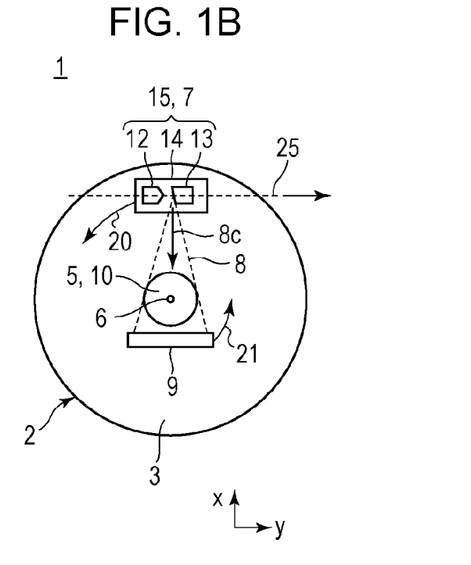
Figure 1C:
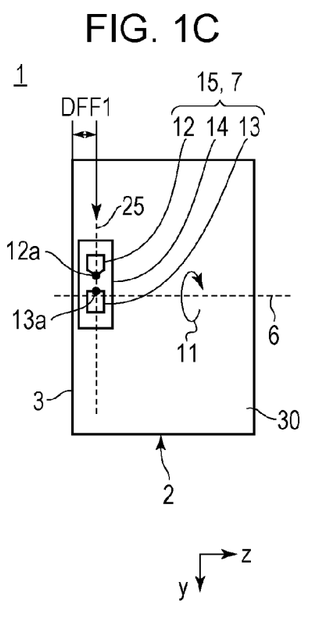
Figure 1D:
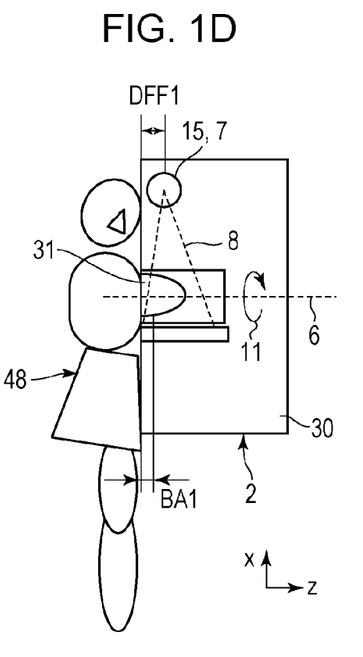
FIG. 1D is a side view of a photographing posture.

FIGS. 1A to 1C are views illustrating arrangement of components of a breast tomography system 1 according to the first embodiment viewed from three angles, respectively. FIG. 1D is a side view of the photographing posture of a subjectee 48 of the breast tomography system 1 of the present embodiment. In FIG. 1D, illustration of the arms of the subjectee 48 is omitted for easy understanding.

The breast tomography system 1 includes, as illustrated in FIGS. 1A and 1B, an X-ray generation tube 15 including a reflection type target 13 and an electron emission source 12. The reflection type target 13 is irradiated with electrons and thereby generates an X-ray. The electron emission source 12 irradiates the reflection type target 13 with an electron beam. The breast tomography system 1 also includes an X-ray detector 9 and a gantry 2. The X-ray detector 9 detects an X-ray emitted from the reflection type target 13 and transmitted through a breast 31. The gantry 2 has a storing space 30 in which the X-ray generation tube 15 and the X-ray detector 9 are stored and has a front panel 3 on the subjectee 48 side. The breast tomography system 1 further includes a rotation drive unit 72 and a breast insertion portion 5 which is communicated through an opening provided in the front panel 3. The rotation drive unit 72 performs rotation 20 (11) on the X-ray generation tube 15 around an imaginary rotation axis 6. The breast 31 can be inserted into the breast insertion portion 5 through the opening 10 coaxially with respect to the imaginary rotation axis 6. Each of the opening 10 and the breast insertion portion 5 is overlapped with the imaginary rotation axis 6, respectively. Each of the opening 10 and the breast insertion portion 5 is located coaxially with respect to the imaginary rotation axis 6.

As illustrated in FIGS. 1A, 1B, and 1D, the X-ray generation tube 15 is disposed in such a manner that the breast insertion portion 5, the breast 31, and the X-ray detector 9 are irradiated with an X-ray flux 8 so that the X-ray detector 9 (described later) detects an X-ray transmission image of the breast 31. A collimator (not illustrated) determines the irradiation angle and an irradiation center axis 8c of the X-ray flux 8. Coaxially setting the irradiation center axis 8c with the imaginary rotation axis 6 enables a wide photographing field for obtaining a tomographic image of the breast 31.

The X-ray detector 9 has a plurality of X-ray detection devices (not illustrated) arranged to detect the X-ray transmitted through the breast 31 located in the breast insertion portion 5. The X-ray detector 9 is secured to the rotation drive unit 72 for rotation 21 (11) around the imaginary rotation axis 6 in the same manner as in the X-ray generation tube 15.

The rotation drive unit 72 includes a rotation supporting member 70 and a motor 71 to rotate the X-ray generation tube 15 and the X-ray detector 9 around the common rotation axis 6 at the same angular velocity. The inclusion of the rotation drive unit 72 in the breast tomography system 1 according to the present embodiment enables the X-ray generation tube 15 to expose the breast 31 to the X-ray flux 8 at different angles and thus enables the X-ray detector 9 to acquire a plurality of original images each having different phase information.

A layout relationship between an X-ray generation tube and a front panel in which the breast tomography system according to the invention in the present application is characterized will next be described.

In the breast tomography system 1 according to the present embodiment, a tube axis 25 of the X-ray generation tube 15 extends parallel to the front panel 3. Specifically, the X-ray generation tube 15 is secured to the rotation drive unit 72 in such a manner that the tube axis 25 of the X-ray generation tube 15 extends along the front panel 3. In the Specification for the present application, a direction in which the tube axis 25 extends (extending direction) is hereinafter explained by using components of the X-ray generation tube 15. The extending direction is determined based on an imaginary line extending from the center of an electron emission unit 12a to the center of a focal spot 13a, as illustrated in FIG. 10.

Here, factors determining the sizes of an X-ray generation tube in an axial direction and a radial direction are described. The cathode of the X-ray generation tube includes an electron gun having a converging lens electrode and an electrostatic lens electrode such as an extraction grid electrode. The cathode has a predetermined length and extends toward an anode. Accordingly, the lower limit of the length of the cathode along the tube axis is restricted by a length of the electron gun.

The anode of the X-ray generation tube having a reflection type target and anode members, such as an anode stem having a heat capacity, a heat sink for heat release from the target, and a rotary drive mechanism that is provided as necessary. The lower limit of the anode along the tube axis is restricted by the anode members connected to the reflection type target. Accordingly, the X-ray generation tube and an X-ray generator including the X-ray generation tube stored in a container are generally shaped to be longer in the axial direction than in the radial direction.

FIGS. 8A, 8B, 8C, and 8D illustrate a breast tomography apparatus 101 as a reference example according to a configuration in the related art, the breast tomography apparatus 101 including a gantry 2 and an X-ray generation tube 15 having the tube axis 25 extending perpendicular to the front panel 3. In the breast tomography apparatus 101 in the reference example, the tube axis 25 is disposed to cross the front panel 3, and a focal spot 23a is thus at a distance DFF2 from the front panel 3. As the result, a blind length BA2 in the reference example is long by being influenced by a distance between the focal spot 23a and an edge portion on the cathode side of the X-ray generation tube 15. In other words, in the breast tomography apparatus 101 in the reference example, the blind length BA2 is long due to the length of the X-ray generation tube 15 on the cathode side of the X-ray generation tube 15 in the extending direction of the tube axis 25. Note that in the side view as in FIG. 1D, the blind length is determined based on the maximum distance between the edge of an opening 10 and the edge of a region that is not irradiated with the X-ray flux 8 on the opening 10 side of the breast insertion portion 5.

Note that also in a reference embodiment (not illustrated) in which the tube axis 25 extends in a direction (−Z direction) antiparallel to the direction in the reference example and crosses the front panel 3, the length, in the axial direction, of the anode members causes a long blind length, as in the foregoing reference example of the X-ray generation tube 15.

In contrast, in the first embodiment illustrated in FIGS. 1A to 1D, the tube axis 25 is disposed to extend along the front panel 3 as illustrated in FIG. 10, and the focal spot 13a is thus at a distance DFF1 from the front panel 3. As the result, as illustrated in FIG. 1D, a blind length BA1 in the present embodiment is shorter than a blind length BA2 in the reference example because a distance between the focal spot 13a and a point corresponding to a half point of the diameter of the X-ray generation tube 15 is shorter than half of the length of the tube axis 25. In other words, since the blind length BA1 is not influenced by the length of the tube axis 25 of the X-ray generation tube 15, the breast tomography system 1 in the present embodiment has the blind length BA1 that is only a short length.

The breast tomography system 1 according to the present embodiment can perform tomography with a decreased blind length on a breast without forcing the subjectee 48 to lie in an unnatural photographing posture.

Figure 9:
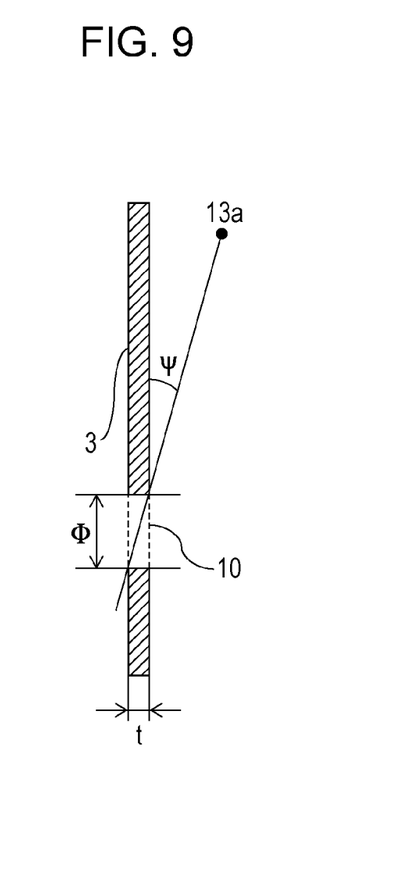
FIG. 9 is a local sectional view of the breast tomography system according to the first embodiment.

FIG. 9 is a view obtained by enlarging a part of FIG. 10 to illustrate a relationship between the front panel 3 and an X-ray flux that generates a leak X-ray near the opening 10 of the front panel 3. The following general formula (1) is used to provide the condition for the X-ray transmitted through the opening 10 having an opening diameter Φ that is provided in the front panel 3 having a thickness t. An angle Ψ represents an upper limit of the skew of the leak X-ray passing through the opening 10. As illustrated in FIG. 9, if the angle Ψ between the front panel 3 and an imaginary line connecting the center of the focal spot 13a and a portion, of the opening 10, farthest from the center of the focal spot 13a satisfies the following general formula (1), the X-ray leaking on the subjectee side through the opening 10 can be reduced.

In other words, the upper limit of the angle Ψ between the imaginary line and the front panel 3 corresponds to a condition for preventing the chest of the subjectee 48 from being exposed to the X-ray flux 8 partially passing through the opening 10.

$$0 \leq \Psi \leq \tan^{-1}(t/\Phi) \quad (1)$$

The opening diameter Φ corresponds to a diameter of the opening 10, and a range from 100 mm to 300 mm is set for the opening diameter Φ to allow the breast 31 of the subjectee 48 to be inserted into the opening 10. Although the thickness t of the front panel 3 is omitted in FIGS. 1A, 10, and 1D, a range from 2 mm to 20 mm is set for the thickness t. The lower limit of the thickness t is determined in consideration for the X-ray attenuation performance or the strength for deformation prevention, and the upper limit of the thickness t is determined in consideration for decrease in blind length. Accordingly, the angle Ψ between the front panel 3 and the tube axis 25 is preferably not smaller than −20 degrees and not larger than +20 degrees, more preferably not smaller than −5 degrees and not larger than +5 degrees, and further preferably not smaller than −1.5 degrees and not larger than +1.5 degrees.

The front panel 3 of the gantry 2 includes the opening 10 communicating with the breast insertion portion 5. It can also be said that the gantry 2 serving as a holder for the breast tomography system 1 and a user interface with the subjectee 48. To secure the photographing posture of the subjectee 48, the gantry 2 is fixed on the floor in such a manner that the breast insertion portion 5 is set at a predetermined height from the floor (not illustrated in FIGS. 1A to 1D) and that the front panel 3 makes a predetermined angle with a vertical plane of the front panel 3.

Second Embodiment and Third Embodiment

Figure 2A:
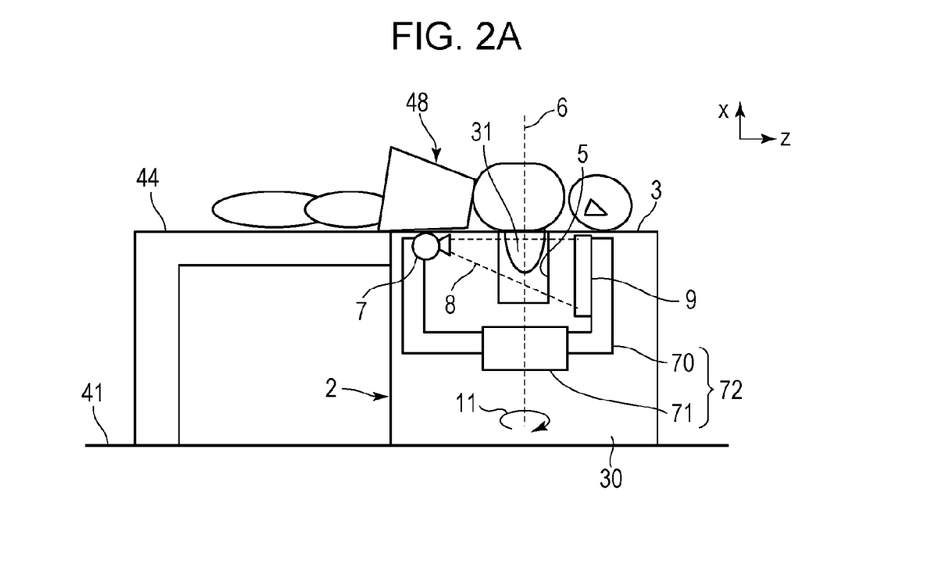
FIGS. 2A and 2B are side views of photographing postures on breast tomography systems according to a second embodiment and a third embodiment, respectively.
Figure 2B:
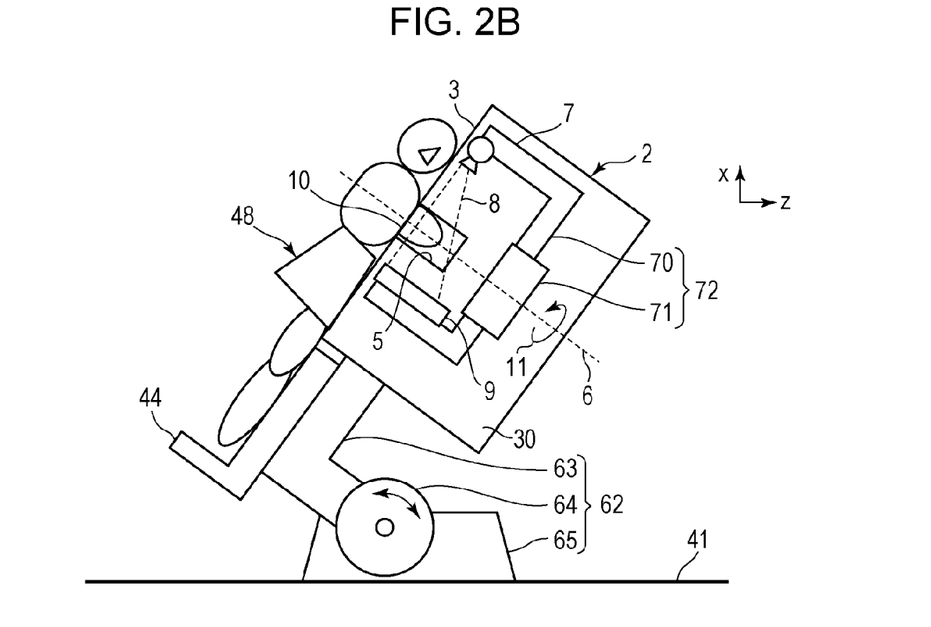

Breast tomography systems 1 according to second and third embodiments, respectively, of the present invention will next be described by using FIGS. 2A and 2B. FIGS. 2A and 2B illustrate photographing postures of the subjectee 48 on the respective breast tomography systems 1 according to the second and third embodiments. FIGS. 2A and 2B each also illustrate a connection relationship among a foot rest 44, the gantry 2, and a floor 41, the foot rest 44 being omitted in FIGS. 1A to 1D illustrating the first embodiment.

In the breast tomography system 1 in the second embodiment illustrated in FIG. 2A, the gantry 2 is installed on the floor 41 in such a manner that the front panel 3 extends along a horizontal plane (yz plane) and that the imaginary rotation axis 6 extends vertically (in an X-direction) so that the subjectee 48 can lie with the face down in the photographing posture. The breast tomography system 1 of the present embodiment includes the foot rest 44 continuous to the front panel 3, and the front panel 3 and the foot rest 44 form a test bed.

The breast tomography system 1 in the third embodiment that is illustrated in FIG. 2B includes a posture change unit 62 that changes the photographing posture of the subjectee 48 in succession from the standing position to a procumbent position. The gantry 2 and the foot rest 44 in the present embodiment are installed on the floor 41 with the posture change unit 62 placed therebetween. The posture change unit 62 includes a joint supporting portion 63, a rotary unit 64, and a base unit 65 and can change the positions of the front panel 3 and the foot rest 44 in an integrated manner to make an angle with the floor 41 from a vertical angle to a perpendicular angle.

Also in the second and third embodiments, as in the first embodiment, the X-ray generation tube 15 is connected to the rotation drive unit 72 in such a manner as to be rotated around the imaginary rotation axis 6 with the tube axis 25 maintained parallel to the front panel 3. In each of the second and third embodiments, the tube axis 25 is disposed to extend along the front panel 3 as in the first embodiment, and tomography with a decreased blind length thus can be performed on a breast without forcing the subjectee 48 to lie in an unnatural photographing posture.

Fourth Embodiment

A breast tomography system 1 according to a fourth embodiment and a modification of the present invention will next be described by using FIGS. 3A, 3B, 3C, and 3D. In the present embodiment, electrical connection between the X-ray generation tube 15 and an X-ray tube voltage circuit 17, a container 18 that stores the X-ray generation tube 15 and the X-ray tube voltage circuit 17, and a grounding scheme for the container 18 and the gantry 2 are illustrated. Illustration of these has been omitted in the first embodiment. In FIGS. 3A to 3D, the X-ray detector, the breast insertion portion, the opening, and the rotation drive unit are appropriately omitted for easy understanding, as in FIGS. 1A to 1D.

Figure 3A:
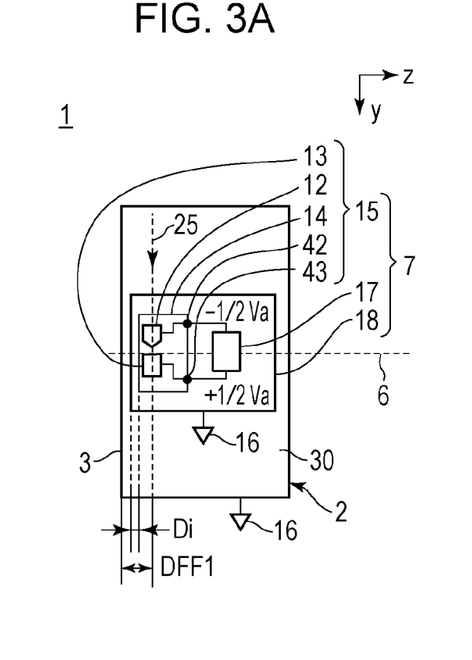
FIGS. 3A and 3B are views of a breast tomography system according to a fourth embodiment viewed from two angles, respectively.
Figure 3B:
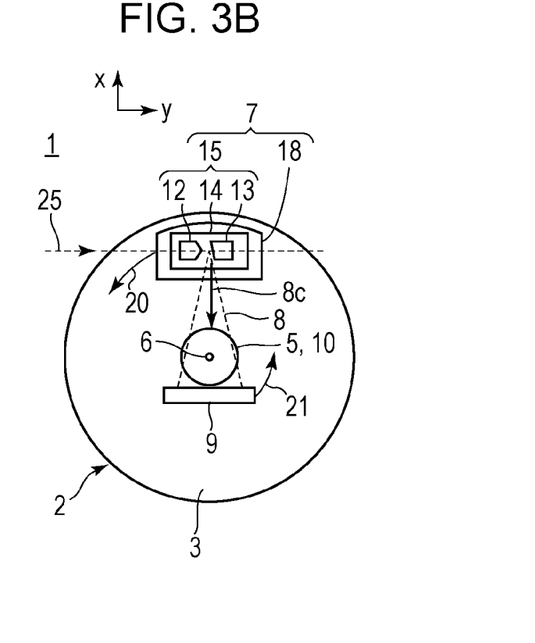
Figure 3C:
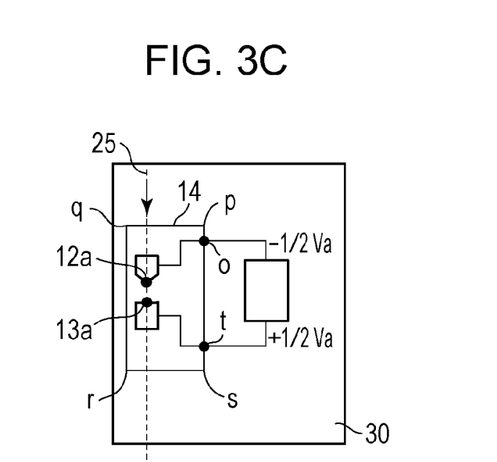
FIG. 3C is an enlarged fragmentary view of the breast tomography system.
Figure 3D:
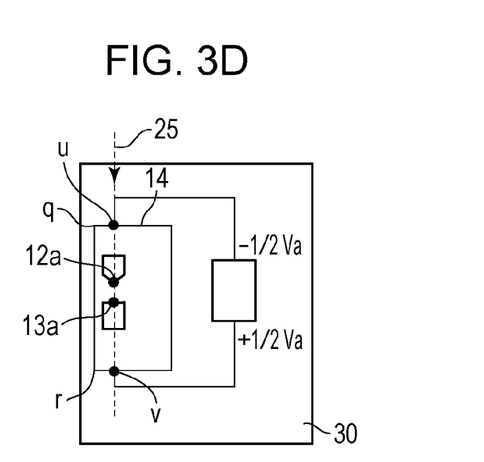
FIG. 3D is an enlarged fragmentary view of the breast tomography system according to a modification of the fourth embodiment.

The breast tomography system 1 in the fourth embodiment includes an X-ray generation source 7 including the X-ray generation tube 15 that has the stationary reflection type target 13, the X-ray tube voltage circuit 17 that applies an X-ray tube voltage Va, and the metal container 18 that stores the X-ray generation tube 15 and the X-ray tube voltage circuit 17. FIG. 3D illustrates the modification of the fourth embodiment that is different from the fourth embodiment in the position of electrical connection between the X-ray generation tube 15 and the X-ray tube voltage circuit 17.

The electric potential of the X-ray generation tube 15 in each of the fourth embodiment and the modification is regulated with respect to the X-ray tube voltage circuit 17 by using a neutral grounding manner. The gantry 2 and the container 18 are electrically connected to a ground terminal 16, and the electric potentials thereof are each regulated to be a ground potential. The electric potential of the reflection type target 13 is regulated to be +½×Va. In other words, the electric potential of the reflection type target 13 is more positive than the ground potential and takes on a smaller absolute value than the X-ray tube voltage Va. Likewise, the electric potential of the electron emission source 12 is regulated to be −½×Va. In other words, the electric potential of the electron emission source 12 is more negative than the ground potential and takes on a smaller absolute value than the X-ray tube voltage Va.

The anode including the reflection type target 13 is connected to an anode output terminal of the X-ray tube voltage circuit 17 with an anode terminal 43 placed therebetween, and the cathode including the electron emission source 12 is connected to a cathode output terminal of the X-ray tube voltage circuit 17 with a cathode terminal 42 placed therebetween. The cathode terminal 42 and the anode terminal 43 are arranged, in the X-ray generation tube 15, in a portion away from the front panel 3 in consideration for a withstand voltage. It can also be said that the cathode terminal 42 and the anode terminal 43 are located father from the front panel 3 than the tube axis 25 determined by the electron emission unit 12a and the focal spot 13a.

Hereinafter, the arrangement of the cathode terminal 42 and the anode terminal 43 in the X-ray generation tube 15 and a potential difference ΔVqr on the front panel 3 side of an envelope 14 of the X-ray generation tube 15 will next be described by using FIGS. 3C and 3D and general formulae (2), (3), (4), and (5). As illustrated in FIGS. 3C and 3D, positions o, p, q, r, s, t, u, and v are set on a creepage surface of the envelope 14. Among these, the positions s and t are the positions of connection terminals in the present embodiment illustrated in FIGS. 3A and 3C and are located farther from the front panel 3 than from the tube axis 25. The positions u and v are the positions of connection terminals in the modification illustrated in FIG. 3D and are located on an imaginary line extending from the tube axis 25. The positions q and r correspond to a section facing the container 18 on the front panel 3 side of the envelope 14. The potential difference ΔVqr on the front panel 3 side of the envelope 14 is determined, as in the general formula (2), by using a capacitance division ratio of the X-ray tube voltage Va on a creepage surface of an insulating member of the envelope 14, and the capacitance division ratio is approximated by using a ratio of a creepage distance for insulation.

$$\Delta Vqr = \text{capacitance division ratio} \times \text{X-ray tube voltage } Va \text{ ratio of creepage distance for insulation} \times \text{X-ray tube voltage } Va \quad (2)$$

Potential differences ΔVqr(c) and ΔVqr(d) on the front panel 3 side of the envelope 14 in the present embodiment and the modification illustrated in FIGS. 3C and 3D are expressed by the following general formulae (2) and (3), respectively.

$$\Delta Vqr(c) = (\text{creepage distance for insulation } qr)/(\text{creepage distance for insulation } opqrst) \times \text{X-ray tube voltage } Va \quad (3)$$

$$\Delta Vqr(d) = (\text{creepage distance for insulation } qr)/(\text{creepage distance for insulation } uqrv) \times \text{X-ray tube voltage } Va \quad (4)$$

The general formula (5) is derived from the general formulae (3) and (4).

$$\Delta Vqr(c) < \Delta Vqr(d) \quad (5)$$

As described above, the cathode terminal 42 and the anode terminal 43 are disposed farther from the front panel 3 than from the tube axis 25. In the creepage distance for insulation between the cathode terminal 42 and the anode terminal 43 in the envelope 14, a creepage distance for insulation on a surface of the envelope 14 is thus reduced, the surface facing the front panel 3. As the result, the arrangement of the cathode terminal 42 and the anode terminal 43 that are farther from the front panel 3 than from the tube axis 25 causes capacitance division and thus reduction in the potential difference ΔVqr on the front panel 3 side of the envelope 14.

This enables the envelope 14 and the container 18 to be close to each other with an insulation distance Di defined therebetween and thus reduces the distance DFF1 from the focal spot formed on the reflection type target 13 to the front panel 3. The blind length can thus be reduced. This can make the insulation distance Di and the distance DFF1 shorter than in a case where the cathode terminal 42 and the anode terminal 43 are disposed on a line extending from the tube axis 25 or on the front panel 3 side.

Accordingly, the breast tomography system 1 according to the fourth embodiment can perform tomography with a decreased blind length on a breast without forcing the subjectee 48 to lie in an unnatural photographing posture.

In the invention in the present application, the neutral grounding manner is defined as a grounding manner in which the electric potential between an anode potential and a cathode potential is grounded and the X-ray tube voltage is applied from the X-ray tube voltage circuit 17 to the X-ray generation tube 15. In the neutral grounding manner, the anode potential is algebraically expressed as +k×Va, and the cathode potential is expressed as +(k−1)×Va, where a constant k is larger than 0 and smaller than 1. To obtain a short insulation distance between the container 18 and the envelope 14, k is preferably not smaller than 0.495 and is not larger than 0.505, and more preferably, k=0.5.

Meanwhile, although not illustrated in FIG. 3A, the container 18 of the X-ray generation source 7 in the present embodiment contains an insulating liquid in such a manner that the insulating liquid is in contact with the X-ray generation tube 15 and the inner wall of the container 18. Examples of an applicable insulating liquid include an insulating oil, such as a mineral oil, a perfluoro oil, or a silicone oil, and sulfur hexafluoride. The insulating liquid contributes to electrical insulation among the X-ray generation tube 15, the container 18, and the X-ray tube voltage circuit 17 and to convection of the X-ray generation tube 15. The X-ray tube voltage circuit 17 may be disposed outside the container 18.

Fifth Embodiment

Figure 4A:
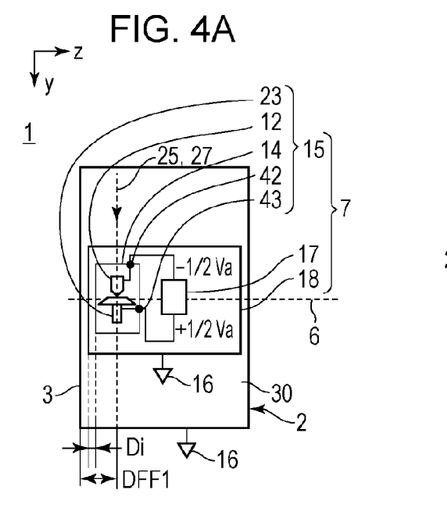
FIGS. 4A and 4B are views of a breast tomography system according to a fifth embodiment viewed from two angles, respectively.
Figure 4B:
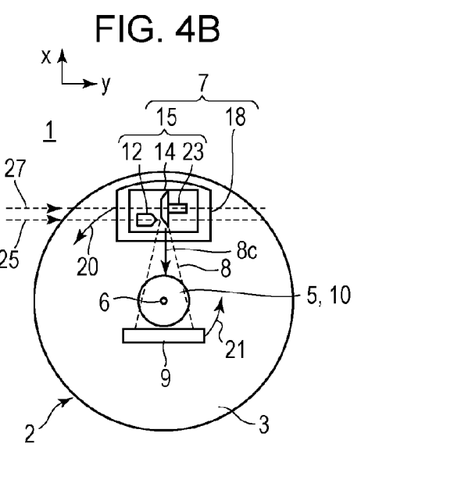

A breast tomography system 1 according to a fifth embodiment of the present invention and a modification of the fifth embodiment will next be described by using FIGS. 4A, 4B, 4C, and 4D. The fifth embodiment illustrated in FIGS. 4A and 4B is different from the fourth embodiment in that a reflection type target 23 has a rotary anode and that the focal spot of the reflection type target 23 having the rotary anode is offset toward the X-ray detector 9 and makes focal tracks on the reflection type target 23. In the Specification in the present application, the reflection type target having the rotary anode is hereinafter referred to as a rotary anode, for simplicity. In FIGS. 4A to 4D, the X-ray detector, the breast insertion portion, the opening, and the rotation drive unit are appropriately omitted for easy understanding, as in FIGS. 3A and 3B. The focal tracks of the present embodiment distribute in the conical and trapezoidal area on the conical surface of the rotary anode 23.

In the fifth embodiment, a focal spot 23a is disposed in the focal tracks so as to maximize a solid angle made by the focal spot 23a with the X-ray detector 9. In other words, in the present embodiment, the electron emission source 12 and the rotary anode 23 are arranged so as to maximize the solid angle made by the focal spot 23a with the X-ray detector 9. The arrangement of the focal spot 23a as in the present embodiment maximizes the intensity of the X-ray to which the breast insertion portion 5 is exposed under the constant tube current condition and thus reduces thermal load on the rotary anode 23.

To achieve the arrangement of the focal spot 23a in the present embodiment, as illustrated in FIG. 4B, the electron emission source 12 is disposed in such a manner that the tube axis 25 is closer than an anode rotation axis 27 of the rotary anode 23 to the X-ray detector 9. Also to achieve the arrangement of the focal spot 23a in the present embodiment, as illustrated in FIG. 4A, a distance between the anode rotation axis 27 of the rotary anode 23 and the front panel 3 is equal to a distance between the tube axis 25 and the front panel 3.

The breast tomography system 1 according to a modification of the fifth embodiment of the present invention will next be described by using FIGS. 4C to 4E. The modification is different from the fifth embodiment illustrated in FIGS. 4A and 4B in that a focal spot is formed at a point, on the rotary anode 23, closest to the front panel 3 and makes focal tracks. In the modification as illustrated in FIG. 4E, the electron emission unit 12a and the focal spot 23a are disposed to be closer than the anode rotation axis 27 of the rotary anode 23 to the front panel 3, and the proximity of the focal spot 23a to the front panel 3 can provide reduction in blind length on the chest side. Since the solid angle made by the focal spot 23a with the X-ray detector 9 is restricted in the modification in comparison with the fifth embodiment, the intensity of the X-ray to which the breast insertion portion 5 is exposed is reduced, but the apparent size of the focal spot viewed from the X-ray detector 9 can be reduced.

Figure 4C:
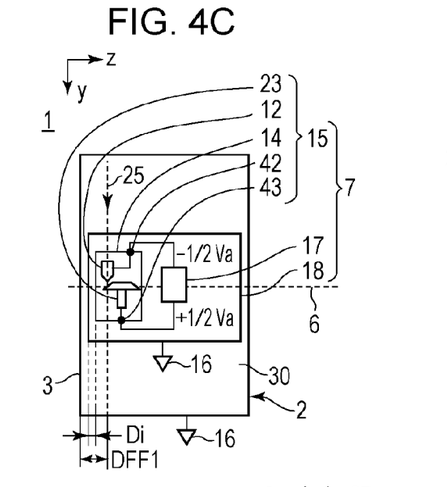
FIGS. 4C and 4D are views of the breast tomography system according to a modification of the fifth embodiment viewed from two angles, respectively.
Figure 4D:
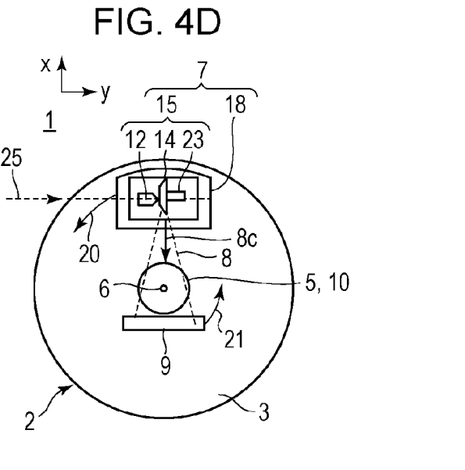
Figure 4E:
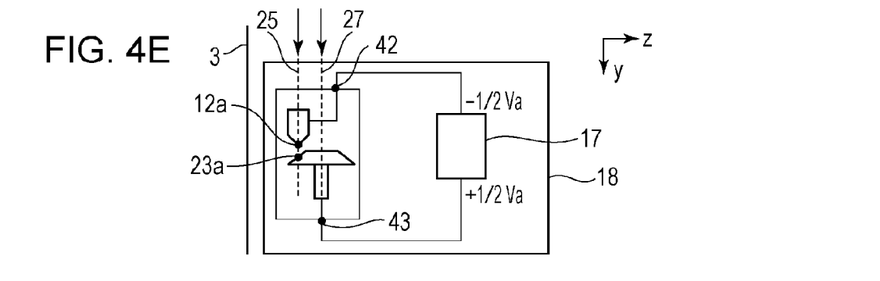
FIG. 4E is an enlarged view of the breast tomography system according to the modification.
Figure 5A:
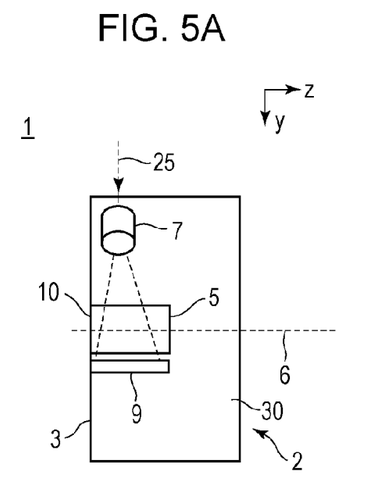
FIGS. 5A and 5B are views of a breast tomography system according to a sixth embodiment viewed from two angles, respectively.
Figure 5B:
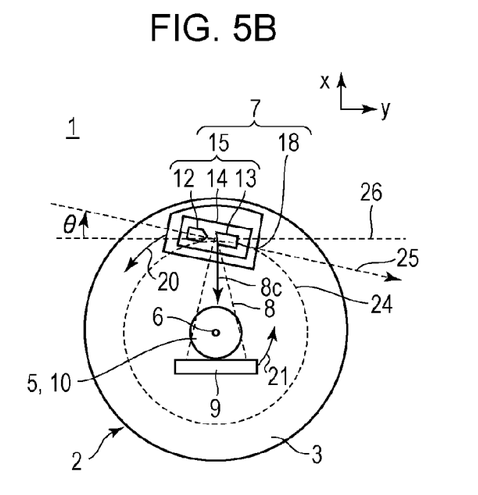
Figure 5C:
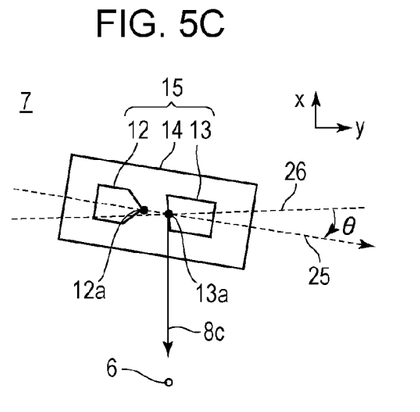
FIG. 5C is an enlarged view of an X-ray generation source.
Figure 5D:
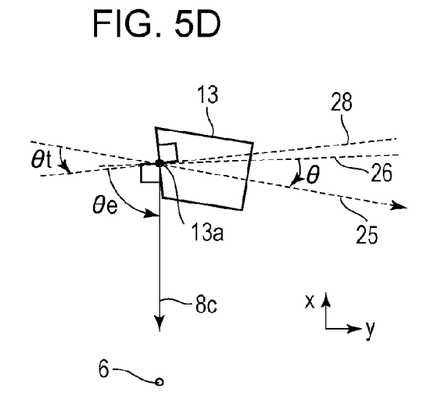
FIG. 5D is an enlarged view of a reflection type target.
Figure 6A:
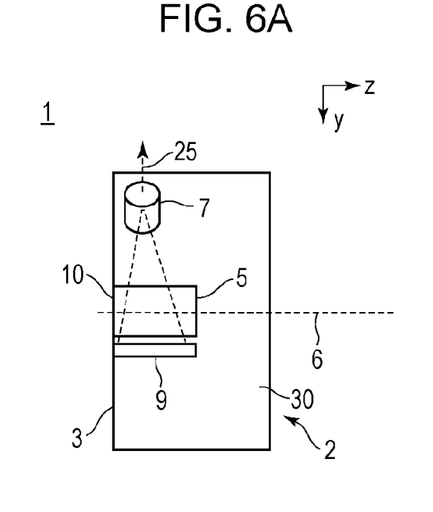
FIGS. 6A and 6B are views of a breast tomography system according to a seventh embodiment viewed from two angles, respectively.
Figure 6B:
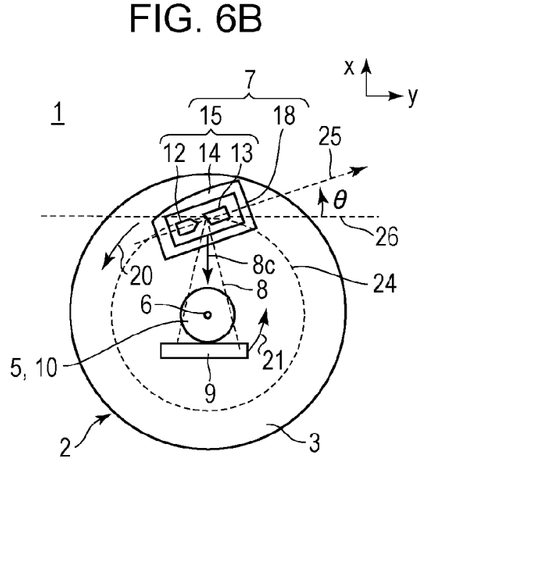
Figure 6C:
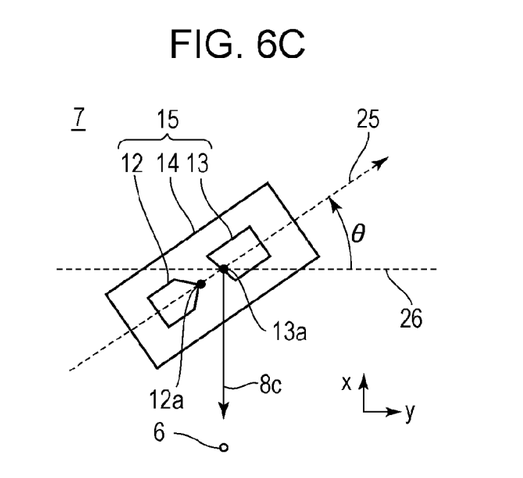
FIG. 6C is an enlarged view of an X-ray generation source.
Figure 6D:
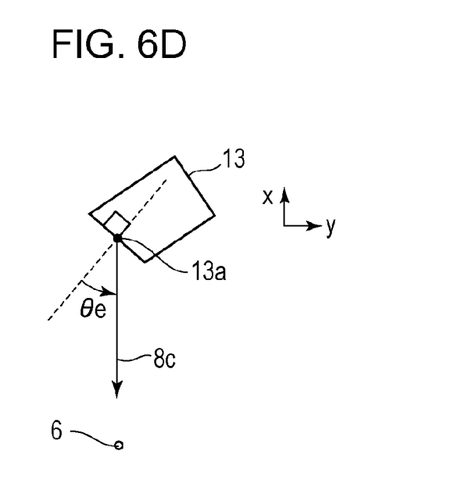
FIG. 6D is an enlarged view of a reflection type target.

In each of the fifth embodiment and the modification as illustrated in FIGS. 4A and 4C, like the fourth embodiment, the cathode terminal 42 and the anode terminal 43 are disposed farther from the front panel 3 than from the tube axis 25, and the X-ray generation tube 15 thus can be made close to the front panel 3 side of the container 18. As the result, the breast tomography apparatuses 1 according to the fifth embodiment and the modification can perform tomography with a decreased blind length on a breast without forcing the subjectee 48 to lie in an unnatural photographing posture.

Sixth Embodiment

A breast tomography system 1 according to a sixth embodiment of the present invention will next be described by using FIGS. 5A, 5B, 5C, and 5D. FIGS. 5A to 5D illustrate a representative relationship between the gantry 2 and the X-ray generation tube 15 that is located at the top position of a scan trajectory 24 of the focal spot 13a. However, the technical significance of the present embodiment (described later) is generalized and does not depend on the position of the X-ray generation tube 15 in the gantry 2 at the time of scanning.

The present embodiment has arrangement similar to that of the first embodiment in terms of a positional relationship in which the extending direction of the tube axis 25 of the X-ray generation tube 15 is parallel to the front panel 3 and is perpendicular to the imaginary rotation axis 6. Accordingly, the breast tomography system 1 according to the present embodiment can perform tomography with a decreased blind length on a breast without forcing the subjectee 48 to lie in an unnatural photographing posture.

Nevertheless, the present embodiment is different from the first embodiment illustrated in FIGS. 1A to 1D in that among the planes tangent to the focal spot 13a on the scan trajectory 24, tube axis 25 of the X-ray generation tube 15 extends closer than a tangent plane 26, which is parallel to the imaginary rotation axis 6, to the inside of the scan trajectory 24. In other words, in the present embodiment, the electron emission unit 12a is located outward of the focal spot 13a in a radial direction of the gantry 2.

In comparison with the first embodiment, the present embodiment in such arrangement has a decreased apparent diameter of the focal spot 13a formed on the reflection type target 13 and improved resolution of a photographed image in the radial direction of the gantry 2. When an angle between a normal line of an electron incident surface of the reflection type target 13 and the tube axis 25 is denoted by θt, and when an angle between the tube axis 25 and the tangent plane 26 is denoted by θ, an emission angle θe of the irradiation center axis 8c extending to the imaginary rotation axis 6 is expressed by using the following general formula (6).

$$\theta e = 90 \text{ degrees} - (\theta t - \theta) \quad (6)$$

When the diameter, in parallel with the front panel 3, of the focal spot 13a formed on the electron incident surface of the reflection type target 13 is denoted by Φ, the apparent focal spot diameter viewed from the X-ray detector 9 is Φ×cos (θe). Accordingly, in the present embodiment in which among the planes tangent to the focal spot 13a on the scan trajectory 24, tube axis 25 of the X-ray generation tube 15 extends closer than the tangent plane 26, which is parallel to the imaginary rotation axis 6, to the inside of the scan trajectory 24 and makes an angle of θ with the tangent plane 26, the apparent focal spot diameter in the gantry radial direction along the front panel 3 is reduced.

Note that the apparent diameter of the focal spot 13a corresponds to the solid angle made by the X-ray detector 9 and is measured with a pinhole mask (not illustrated) disposed between the reflection type target 13 and the X-ray detector 9. In addition, the emission angle θe is defined with respect to a normal line 28 of the electron incident surface of the reflection type target 13, and the emission angle of zero degrees corresponds to a condition for vertical reflection. The tangent plane 26 is a plane defined by the imaginary rotation axis 6 and a tangent line including the focal spot 13a at any position on the annular scan trajectory 24 that is determined around the imaginary rotation axis 6 by the focal spot 13a.

Seventh Embodiment

A breast tomography system 1 according to a seventh embodiment of the present invention will next be described by using FIGS. 6A, 6B, 6C, and 6D. FIGS. 6A to 6D illustrate a representative relationship between the gantry 2 and the X-ray generation tube 15 that is located at the top position of the scan trajectory 24 of the focal spot 23a. However, the technical significance of the present embodiment (described later) is generalized and does not depend on the position of the X-ray generation tube 15 in the gantry 2 at the time of scanning.

The present embodiment has arrangement similar to that of the first embodiment in terms of a positional relationship in which the extending direction of the tube axis 25 of the X-ray generation tube 15 is parallel to the front panel 3 and is perpendicular to the imaginary rotation axis 6. Accordingly, the breast tomography system 1 according to the present embodiment can perform tomography with a decreased blind length on a breast without forcing the subjectee 48 to lie in an unnatural photographing posture.

Nevertheless, the present embodiment is different from the first and sixth embodiments in that among the planes tangent to the focal spot 13a on the scan trajectory 24, tube axis 25 of the X-ray generation tube 15 extends closer than the tangent plane 26, which is parallel to the imaginary rotation axis 6, to the outside of the scan trajectory 24. In other words, in the present embodiment, the electron emission unit 12a is located inward of the focal spot 13a in the radial direction of the gantry 2.

In comparison with the first and sixth embodiments, the present embodiment in such arrangement has reduced X-ray output intensity and reduced dependence of the radiation quality on an emission angle because proximity of the irradiation center axis 8c of the X-ray flux 8 to a normal line of the electron incident surface causes reduction in the emission angle θe. Accordingly, in the seventh embodiment, the reduction in the X-ray output intensity and the reduction in the dependence of the radiation quality on the radiation angle enable the X-ray generation tube 15 and the breast insertion portion 5 to be close to each other and thus provide a merit of size reduction of the gantry 2.

Eighth Embodiment

Figure 7:
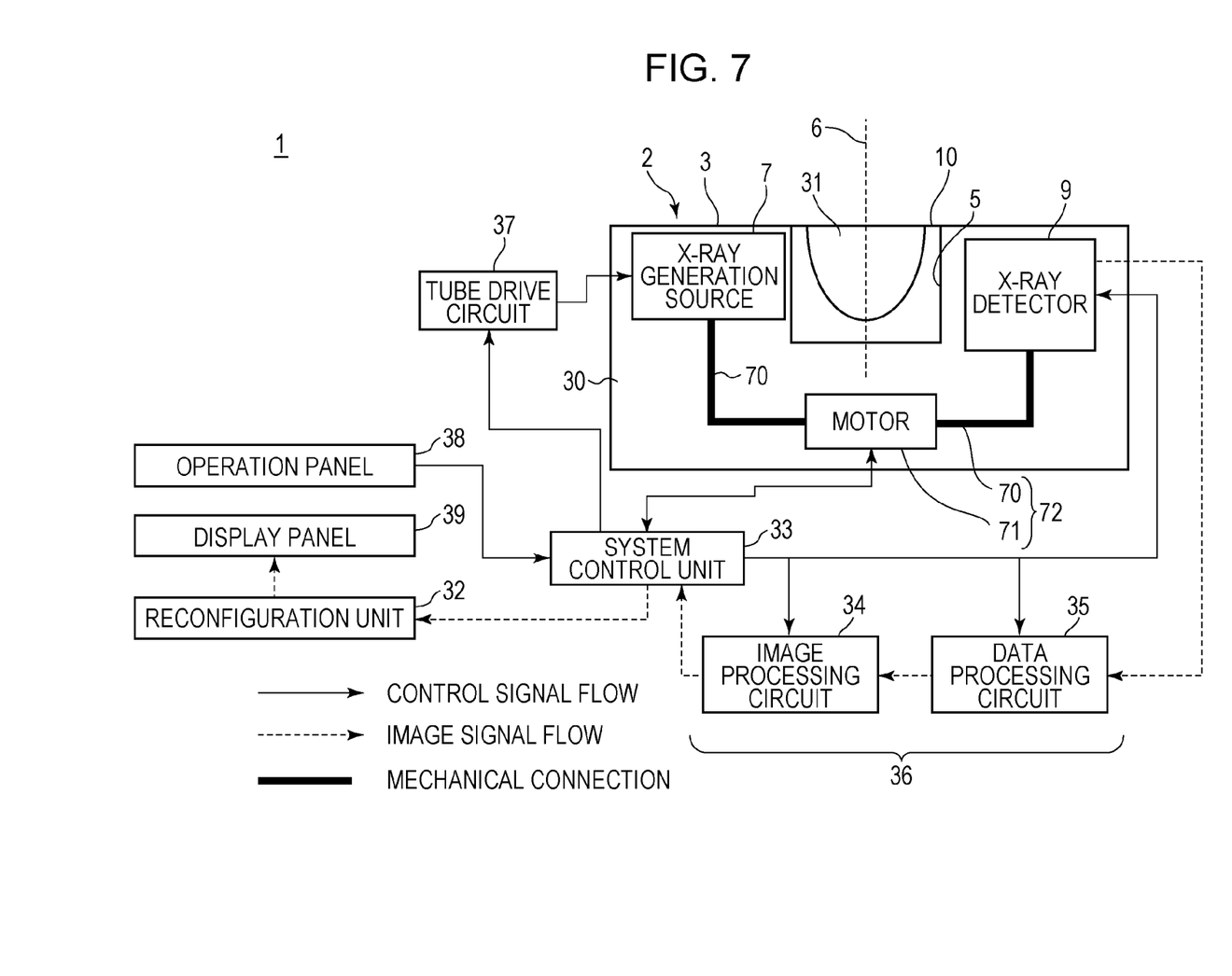
FIG. 7 is a system block diagram of a breast tomography system according to an eighth embodiment.
Figure 8A:
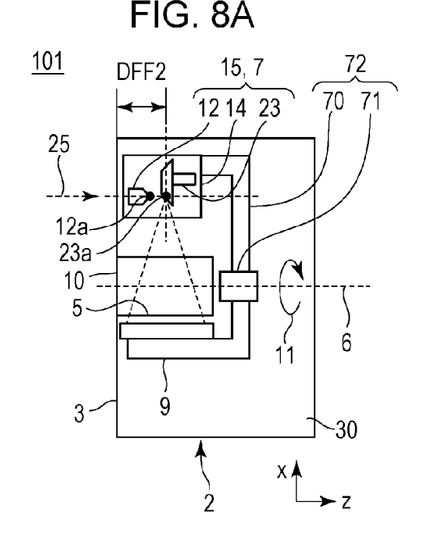
FIGS. 8A, 8B, and 8C are views of a breast tomography system according to a reference example viewed from three angles, respectively.
Figure 8B:
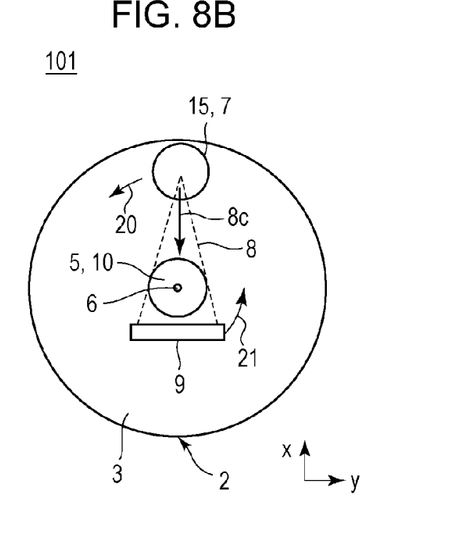
Figure 8C:
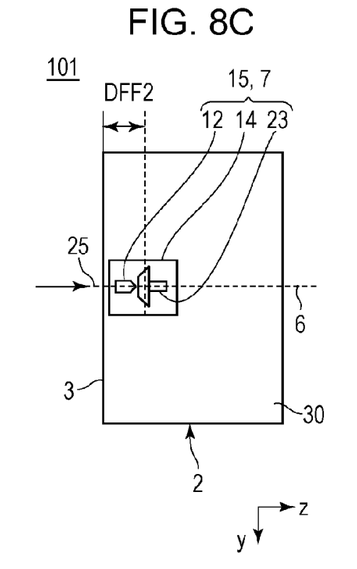
Figure 8D:
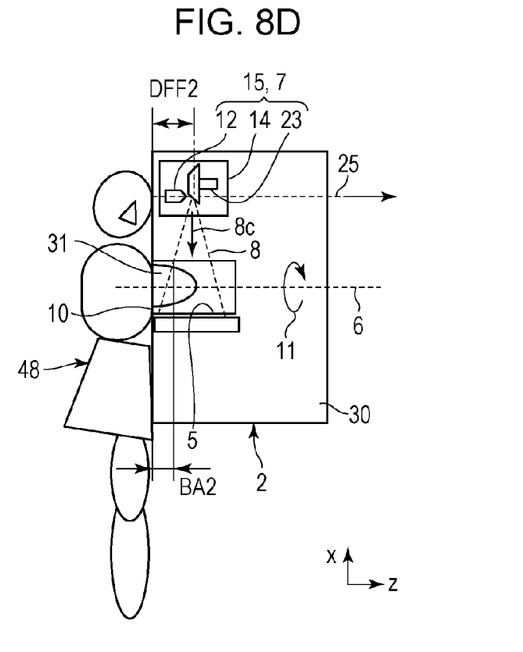
FIG. 8D is a side view of a photographing posture on the breast tomography system.

Tomography performed by a breast tomography system 1 according to an eighth embodiment of the present invention will next be described by using FIG. 7. FIG. 7 illustrates a system block diagram of the breast tomography system 1 that acquires an X-ray tomographic image of the breast 31 by taking a plurality of images at exposure angles around the imaginary rotation axis 6.

Although the axial direction of the X-ray generation tube 15 in the present embodiment is not explicitly illustrated, the X-ray generation tube 15 is connected to the rotation drive unit 72 in such a manner as to be parallel to the front panel 3 in the axial direction and to perform rotation 11 around the imaginary rotation axis 6 in this parallel state, as in the first embodiment.

In the present embodiment, the rotation drive unit 72 in the gantry 2 may be disposed outside the gantry 2. Also in the present embodiment, the X-ray detector 9 may be annularly arranged outside the gantry 2 in the radial direction in such a manner as to extend continuously, without connecting to the rotation supporting member 70. In terms of reduction in scattering X-ray received by the X-ray detector 9 and reduction in semi-shading, it is desirable to dispose the X-ray detector 9 as close to the breast 31 that is a photographic subject as possible on the optical path of the X-ray flux. In this point, as described in the present embodiment and the first to third embodiments, it is desirable to dispose the X-ray detector 9 on the rotation supporting member 70 to be closer than the X-ray generation tube 15 to the imaginary rotation axis 6.

Output from the X-ray detector 9 includes X-ray transmission image data, and a tomographic image is output to a display panel 39 via a signal processor 36, a system control unit 33, and a reconfiguration unit 32. The signal processor 36 includes a data processing circuit 35 and an image processing circuit 34. The output side of the system control unit 33 is connected to a tube drive circuit 37, the X-ray generation tube 15, the rotation drive unit 72, the data processing circuit 35, and the image processing circuit 34. An operation panel 38 is connected to the system control unit 33 to input an operation instruction signal.

In the breast tomography system 1 of the present embodiment, the X-ray generation tube 15 and the X-ray detector 9 are arranged in such a manner as to face each other and rotate around the imaginary rotation axis 6 for scanning in synchronization with each other. The X-ray generation tube 15 makes different angles with the breast 31 that are caused to be changed by the rotation drive unit 72, and X-ray transmission images can thus be acquired according to the respective angles of the X-ray generation tube.

In the breast tomography system of the present invention, the reflective X-ray generation tube is disposed in such a manner as to extend along the front panel of the gantry. Accordingly, with the breast tomography system of the invention in the present application, a distance between the focal spot formed on the reflection type target and the front panel can be made shorter than in the case of the related art in which the axial direction is set to cross the front panel. The present invention can thus provide a breast tomography system that achieves each of reduction in unnecessary exposure of the chest of a subjectee, reduction in a blind length on the chest side, and improvement in usability.

While aspects of the present invention have been described with reference to exemplary embodiments, it is to be understood that these exemplary embodiments are not seen to be limiting. The scope of the following claims is to be accorded the broadest interpretation so as to encompass all such modifications and equivalent structures and functions.

This application claims the benefit of Japanese Patent Application No. 2014-249441, filed Dec. 9, 2014 and No. 2015-215255 filed Oct. 30, 2015, which are hereby incorporated by reference herein in their entirety.

What is claimed is:

1. A breast tomography system comprising:
    an X-ray generation tube including a reflection type target and an electron emission source, the reflection type target being irradiated with an electron and generating an X-ray, the electron emission source irradiating the reflection type target with an electron beam;
    an X-ray detector that detects the X-ray emitted from the reflection type target and transmitted through a breast;
    a gantry having a storing space in which the X-ray generation tube and the X-ray detector are stored and a front panel between the storing space and a subjectee;
    a rotation drive unit that rotates the X-ray generation tube around an imaginary rotation axis; and
    a breast insertion portion configured to be communicated through an opening provided in the front panel,
    wherein the X-ray generation tube is secured to the rotation drive unit to allow a tube axis of the X-ray generation tube to extend along the front panel, and wherein when an opening diameter of the opening is Φ, and when a thickness of the front panel is t, an angle Ψ between the focal spot and the front panel satisfies the formula below $$0 \leq \Psi \leq \tan^{-1}(t/\Phi).$$

2. The breast tomography system according to claim 1, wherein an angle between the tube axis and the front panel is not smaller than −20 degrees and not larger than +20 degrees.

3. The breast tomography system according to claim 2, wherein the tube axis is disposed substantially parallel to the front panel.

4. The breast tomography system according to claim 1, wherein the X-ray generation tube has, in an outside dimension, a length shorter in a radial direction of the X-ray generation tube than in a direction in which the tube axis extends.

5. The breast tomography system according to claim 1, wherein the tube axis extends toward an inside of the gantry.

6. The breast tomography system according to claim 1, wherein the tube axis extends toward an outside of the gantry.

7. The breast tomography system according to claim 1, wherein the electron emission source includes an electron emission unit that emits an electron beam,
wherein the reflection type target is irradiated with the electron beam, and a focal spot is formed on the reflection type target, and
wherein the direction in which the tube axis extends is determined by a direction in which an imaginary line extends from a center of the electron emission unit to a center of the focal spot.

8. The breast tomography system according to claim 7, wherein the electron emission unit is located outward of the focal spot in a radial direction of the gantry.

9. The breast tomography system according to claim 7, wherein the electron emission unit is located inward of the focal spot in a radial direction of the gantry.

10. The breast tomography system according to claim 1, wherein the X-ray detector is secured to the rotation drive unit to allow the breast insertion portion to face the X-ray generation tube.

11. The breast tomography system according to claim 1, wherein an electric potential of the gantry is regulated to be a ground potential, and a tube voltage is applied to the X-ray generation tube,
wherein an electric potential of the reflection type target is regulated to be more positive than the ground potential and to take on an absolute value smaller than the tube voltage, and
wherein an electric potential of the electron emission source is regulated to be more negative than the ground potential and to take on an absolute value smaller than the tube voltage.

12. The breast tomography system according to claim 11, further comprising:
a portion in which the electric potential of the reflection type target is regulated to be k×Va; and
a portion in which the electric potential of the electron emission source is regulated to be (k−1)×Va,
wherein a constant k is higher than 0 and smaller than 1, and a tube voltage is Va(V).

13. The breast tomography system according to claim 12, wherein the constant k is not smaller than 0.495 and not larger than 0.505.

14. The breast tomography system according to claim 11, further comprising:
a container that stores the X-ray generation tube, that is stored in the gantry, and an electric potential of which is regulated to be the ground potential; and
an insulating liquid that is in contact with the X-ray generation tube and an inner wall of the container.

15. The breast tomography system according to claim 14, wherein the container stores a tube voltage circuit that applies the tube voltage to the X-ray generation tube.

16. The breast tomography system according to claim 15, wherein the tube voltage circuit includes an anode output terminal electrically connected to the reflection type target and a cathode output terminal electrically connected to the electron emission source,
wherein the X-ray generation tube includes an envelope that stores the reflection type target and the electron emission source, and the envelope includes an anode terminal electrically connected to the anode output terminal and a cathode terminal electrically connected to the cathode output terminal, and
wherein the anode terminal and the cathode terminal are located farther than a focal spot and the electron emission unit from the front panel.

17. The breast tomography system according to claim 1, wherein the reflection type target is a rotary anode that pivots around an anode rotation axis disposed to extend along the front panel.

18. The breast tomography system according to claim 17, wherein the anode rotation axis is disposed parallel to the front panel.

19. The breast tomography system according to claim 17, wherein the electron emission source includes an electron emission unit that emits an electron beam,
wherein the reflection type target is irradiated with the electron beam, and a focal spot is formed on the reflection type target, and
wherein the electron emission unit and the focal spot are closer than the anode rotation axis to the front panel.

20. The breast tomography system according to claim 1, wherein each of the opening and the breast insertion portion is overlapped with the imaginary rotation axis, respectively.

21. The breast tomography system according to claim 20, wherein each of the opening and the breast insertion portion is located coaxially with respect to the imaginary rotation axis.

22. The breast tomography system according to claim 1, wherein the X-ray detector is secured to the rotation drive unit configured to rotate around the imaginary rotation axis in a synchronized manner with the X-ray generation tube.

23. The breast tomography system according to claim 1, wherein the rotation drive unit includes a rotation supporting member and a motor to rotate the X-ray generation tube and the X-ray detector around the imaginary rotation axis at the same angular velocity.

24. A breast tomography system comprising:
an X-ray generation tube including a reflection type target and an electron emission source, the reflection type target being irradiated with an electron and generating an X-ray, the electron emission source irradiating the reflection type target with an electron beam;
an X-ray detector that detects the X-ray emitted from the reflection type target and transmitted through a breast;

a gantry having a storing space in which the X-ray generation tube and the X-ray detector are stored and a front panel between the storing space and a subjectee;
a rotation drive unit that rotates the X-ray generation tube around an imaginary rotation axis; and
a breast insertion portion configured to be communicated through an opening provided in the front panel,
wherein the X-ray generation tube is secured to the rotation drive unit to allow a tube axis of the X-ray generation tube to extend along the front panel,
wherein an electric potential of the gantry is regulated to be a ground potential, and a tube voltage is applied to the X-ray generation tube,
wherein an electric potential of the reflection type target is regulated to be more positive than the ground potential and to take on an absolute value smaller than the tube voltage, and
wherein an electric potential of the electron emission source is regulated to be more negative than the ground potential and to take on an absolute value smaller than the tube voltage,
the breast tomography system further comprising:
a portion in which the electric potential of the reflection type target is regulated to be k×Va; and
a portion in which the electric potential of the electron emission source is regulated to be (k−1)×Va,
wherein a constant k is higher than 0 and smaller than 1, and a tube voltage is Va(V).

25. The breast tomography system according to claim 24, wherein the constant k is not smaller than 0.495 and not larger than 0.505.

* * * * *